US00PP30081P2

(12) United States Plant Patent
Mukundan

(10) Patent No.: US PP30,081 P2
(45) Date of Patent: Jan. 8, 2019

(54) ***AGLAONEMA* PLANT NAMED 'MUKCALSUP'**

(50) Latin Name: *Aglaonema hybrida*
Varietal Denomination: MUKCALSUP

(71) Applicant: Parthasarathy Mukundan, Tamil Nadu (IN)

(72) Inventor: Parthasarathy Mukundan, Tamil Nadu (IN)

( * ) Notice: Subject to any disclaimer, the term of this patent is extended or adjusted under 35 U.S.C. 154(b) by 0 days.

(21) Appl. No.: 15/731,899

(22) Filed: Aug. 21, 2017

(51) Int. Cl.
*A01H 5/12* (2018.01)

(52) U.S. Cl.
USPC ..... Plt./376

(58) Field of Classification Search
USPC ..... Plt./376
CPC ... A01H 5/02; A01H 5/00; A01H 5/12; A01H 6/00
See application file for complete search history.

*Primary Examiner* — June Hwu
(74) *Attorney, Agent, or Firm* — C. A. Whealy

(57) ABSTRACT

A new and distinct cultivar of *Aglaonema* plant named 'MUKCALSUP', characterized by its upright and outwardly arching plant habit; freely clumping habit; vigorous and robust growth habit; relatively short internodes giving a compact, dense and full plant form; large dark green-colored leaves with greyed green-colored chevrons, spots and random sectors; leaf petioles that are green white in color with numerous medium to dark green-colored spots; and relative tolerance to low temperatures.

4 Drawing Sheets

Botanical designation: *Aglaonema hybrida.*
Cultivar denomination: 'MUKCALSUP'.

BACKGROUND OF THE INVENTION

The present invention relates to a new and distinct cultivar of *Aglaonema* plant, botanically known as *Aglaonema hybrida* and hereinafter referred to by the name 'MUKCALSUP'.

The new *Aglaonema* plant is the product of a controlled breeding program conducted by the Inventor in Tiruporur, Chennai, India. The objective of the breeding program is to create new compact and dense *Aglaonema* plants with good plant vigor, interesting and unique leaf shapes and variegation patterns, resistance to pathogens and pests and tolerance to low temperatures.

The new *Aglaonema* plant is a naturally-occurring branch mutation of *Aglaonema hybrida* 'Calypso', disclosed in U.S. Plant Pat. No. 17,540. The new *Aglaonema* plant was discovered and selected by the Inventor on Oct. 21, 2011 on a single plant from within a population of plants of 'Calypso' in a controlled nursery environment in Tiruporur, Chennai, India.

Asexual reproduction of the new *Aglaonema* plant by cuttings and divisions in a controlled environment in Tiruporur, Chennai, India since November, 2011 has shown that the unique features of this new *Aglaonema* plant are stable and reproduced true to type in successive generations of asexual reproduction.

SUMMARY OF THE INVENTION

Plants of the new *Aglaonema* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MUKCALSUP'. These characteristics in combination distinguish 'MUKCALSUP' as a new and distinct *Aglaonema* plant:

1. Upright and outwardly arching plant habit.
2. Freely clumping habit.
3. Vigorous and robust growth habit.
4. Relatively short internodes giving a compact, dense and full plant form.
5. Large dark green-colored leaves with greyed green-colored chevrons, spots and random sectors.
6. Leaf petioles that are green white in color with numerous medium to dark green-colored spots.
7. Relatively tolerant to low temperatures.

Plants of the new *Aglaonema* differ primarily from plants of the mutation parent, 'Calypso', in the following characteristics:

1. Plants of the new *Aglaonema* are more vigorous, faster-growing and denser and bushier than plants of 'Calypso'.
2. Plants of the new *Aglaonema* are more freely clumping than plants of 'Calypso'.
3. Leaves of plants of the new *Aglaonema* are more narrow than leaves of plants of 'Calypso'.
4. Plants of the new *Aglaonema* and 'Calypso' differ in leaf coloration as the upper leaf surfaces of plants of 'Calypso' are dark green in color with greyed green-colored chevrons interspersed with distinct golden yellow spots and blotches and the lower leaf surfaces of plants of 'Calypso' are pale green in color with ivory white-colored midrib, spots and splashes while the new *Aglaonema* has leaf coloration of upper surface with dark green-colored leaves with greyed green-colored chevrons, spots and random sectors and lower surface with dark green-colored leaves with green-colored chevrons and spots with light yellow-green-colored random spots.

5. Plants of the new *Aglaonema* and 'Calypso' differ in leaf petiole coloration as leaf petioles of 'Calypso' are pale yellow to ivory white in color with sparse and random green-colored spots on the petiole wings while the new *Aglaonema* has leaf petioles that are green and white in color with numerous medium to dark green-colored spots.

Plants of the new *Aglaonema* can be compared to plants of *Aglaonema crispum* 'B.J. Freeman', disclosed in U.S. Plant Pat. No. 6,857. In side-by-side comparisons plants of the new *Aglaonema* differ primarily from plants of 'B.J. Freeman' in the following characteristics:

1. Plants of the new *Aglaonema* are more freely clumping and denser and fuller than plants of 'B.J. Freeman'.
2. Leaves of plants of the new *Aglaonema* are more outwardly arching than and not as upright as leaves of plants of 'B.J. Freeman'.
3. Leaves of plants of the new *Aglaonema* are smaller than leaves of plants of 'B.J. Freeman'.
4. Plants of the new *Aglaonema* and 'B.J. Freeman' differ in leaf coloration as leaves of plants of 'B.J. Freeman' are dull green in color with dull pale silvery green-colored markings while the new *Aglaonema* has leaf coloration with dark green-colored leaves with greyed green-colored chevrons, spots and random sectors.
5. Plants of the new *Aglaonema* and 'B.J. Freeman' differ in leaf petiole coloration as leaf petioles of plants of 'B.J. Freeman' are solid medium green in color while the new *Aglaonema* has leaf petioles that are green and white in color with numerous medium to dark green-colored spots.
6. Plants of the new *Aglaonema* are more low temperature tolerant than plants of 'B.J. Freeman'.

Plants of the new *Aglaonema* can also be compared to plants of *Aglaonema crispum* X *Aglaonema treubii* 'Camouflage', disclosed in U.S. Plant Pat. No. 13,573. In side-by-side comparisons plants of the new *Aglaonema* differ primarily from plants of 'Camouflage' in the following characteristics:

1. Plants of the new *Aglaonema* are more freely clumping and denser and fuller than plants of 'Camouflage'.
2. Leaves of plants of the new *Aglaonema* are more narrow than leaves of plants of 'Camouflage'.
3. Plants of the new *Aglaonema* and 'Camouflage' differ in leaf coloration as leaves of plants of 'Camouflage' are light green in color with contrasting dark and mid-green chevrons, random dark and mid-green spots and flecks and dark green-colored margins while the new *Aglaonema* has leaf coloration with dark green-colored leaves with greyed green-colored chevrons, spots and random sectors.

BRIEF DESCRIPTION OF THE PHOTOGRAPHS

The accompanying photographs illustrate the overall appearance of the new *Aglaonema* plant showing the colors as true as it is reasonably possible to obtain in colored reproductions of this type. Colors in the photographs may differ slightly from the color values cited in the detailed botanical description which accurately describe the colors of the new *Aglaonema* plant.

The photograph on the first sheet is a side perspective view of a population of typical plants of 'MUKCALSUP' grown in containers.

The photograph on the second sheet is a close-up view of a population of typical plants of 'MUKCALSUP' grown in containers.

The photograph on the third sheet is side comparison view of typical plants of 'Calypso' (left) and 'MUKCALSUP' (right) grown in containers.

The photograph on the fourth sheet is close-up comparison view of the upper surface of typical leaves and petioles of 'Calypso' (top) and 'MUKCALSUP' (bottom).

DETAILED BOTANICAL DESCRIPTION

The aforementioned photographs and following observations and measurements describe plants grown in 2.25-gallon containers in Miami, Fla. during the spring and early summer in a polypropylene-covered shadehouse. Plants were grown under environmental conditions and cultural practices which approximate those generally used in commercial *Aglaonema* production. During the production of the plants, day temperatures ranged from 25° C. to 32° C. and night temperatures ranged from 15° C. to 23° C. Plants were one year old when the photographs and the detailed description were taken. In the following description, color references are made to The Royal Horticultural Society Colour Chart, 2007 Edition, except where general terms of ordinary dictionary significance are used.

Botanical classification: *Aglaonema hybrida* 'MUKCALSUP'.

Parentage: Naturally-occurring branch mutation of *Aglaonema hybrida* 'Calypso', disclosed in U.S. Plant Pat. No. 17,540.

Propagation:

*Type*.—By top cuttings, stem cuttings and divisions.

*Time to initiate roots, summer*.—About 20 to 25 days at temperatures about 30° C. to 35° C.

*Time to initiate roots, winter*.—About 35 to 40 days at temperatures about 25° C. to 30° C.

*Time to produce a rooted young plant, summer*.—About 45 to 50 days at temperatures about 30° C. to 35° C.

*Time to produce a rooted young plant roots, winter*.—About 50 to 55 days at temperatures about 15° C. to 20° C.

*Root description*.—Medium in thickness, fibrous; typically off-white in color, actual color of the roots dependent on substrate composition, water quality, fertilizer, substrate temperature and age of roots.

*Rooting habit*.—Freely branching; dense.

Plant description:

*Plant and growth habit*.—Upright and somewhat outwardly arching plant habit; freely clumping habit; relatively short internodes giving a compact, dense, full and symmetrical habit; vigorous and robust growth habit; developing leaves initially upright, then arching outwardly with development.

*Plant height, from soil level to top of leaf plane*.—About 67.5 cm.

*Plant diameter or spread*.—About 77.5 cm.

*Stem description*.—Clumping habit: Plants of the new *Aglaonema* are freely clumping with about twelve clumps developing per container. Aspect: Mostly upright. Strength: Strong, sturdy; slightly flexible.

Diameter, at the base: About 2.3 cm. Internode length, at the base: About 1.3 cm. Color: Close to 147A to darker than 147A.

Leaf description:

*Arrangement*.—Alternate to whorled; simple.

*Length*.—About 27 cm.

*Width*.—About 14 cm.

*Shape*.—Broadly lanceolate to elliptic.

*Apex*.—Acuminate, straight.

*Base*.—Obtuse.

*Margin*.—Entire; slightly undulate.

*Texture and luster, upper surface*.—Smooth, glabrous; initially glossy and becoming moderately glossy with development.

*Texture and luster, lower surface*.—Smooth, glabrous; initially moderately glossy and becoming slightly glossy with development.

*Venation pattern*.—Pinnate.

*Color*.—Developing leaves, upper surface: Ground color, close to 146A to more green and darker green than 146A; chevrons and spots, close to 191A to more green than 191A. Developing leaves, lower surface: Close to 146B to more green than 146A. Fully expanded leaves, upper surface: Ground color, darker green than 147A; chevrons and spots, close to 191A and 191B; random sectors between chevrons, close to 189A; mid-vein, darker green than 147A, proximally, with random spots, close to 144A to 144B; lateral venation, similar to lamina colors. Fully expanded leaves, lower surface: Ground color, more green and darker green than 147B; chevrons and spots, close to 147B; random spots, close to 157A to 157B; venation, close to 157A to 157B overlain with spots, close to 146A.

*Petioles*.—Aspect: Mostly erect, outwardly arching with development. Length: About 17 cm. Diameter, distal: About 7 mm by 7.5 mm. Diameter, proximal, flattened: About 4.25 cm. Strength: Strong; flexible. Color, distal: Close to 157A to 157B with numerous spots, close to 146A. Color, proximal: Close to 157A to 157B with numerous spots, close to 147A. Wing length: About 10 cm. Wing diameter, base: About 5 mm. Wing texture: Smooth, glabrous; towards the margin, membraneous. Wing color, inner and outer surfaces: Close to 157A to 157B with numerous spots, close to 147A.

Inflorescence description: Inflorescence development has not been observed on plants of the new *Aglaonema* to date.

Disease & pest resistance: Plants of the new *Aglaonema* have not been observed to be resistant to pathogens or pests common to *Aglaonema* to date.

Temperature tolerance: Plants of the new *Aglaonema* have been observed to be relatively low temperature tolerant and to tolerate temperatures ranging from about 10° C. to about 38° C.

It is claimed:

1. A new and distinct *Aglaonema* plant named 'MUKCALSUP' as illustrated and described.

* * * * *

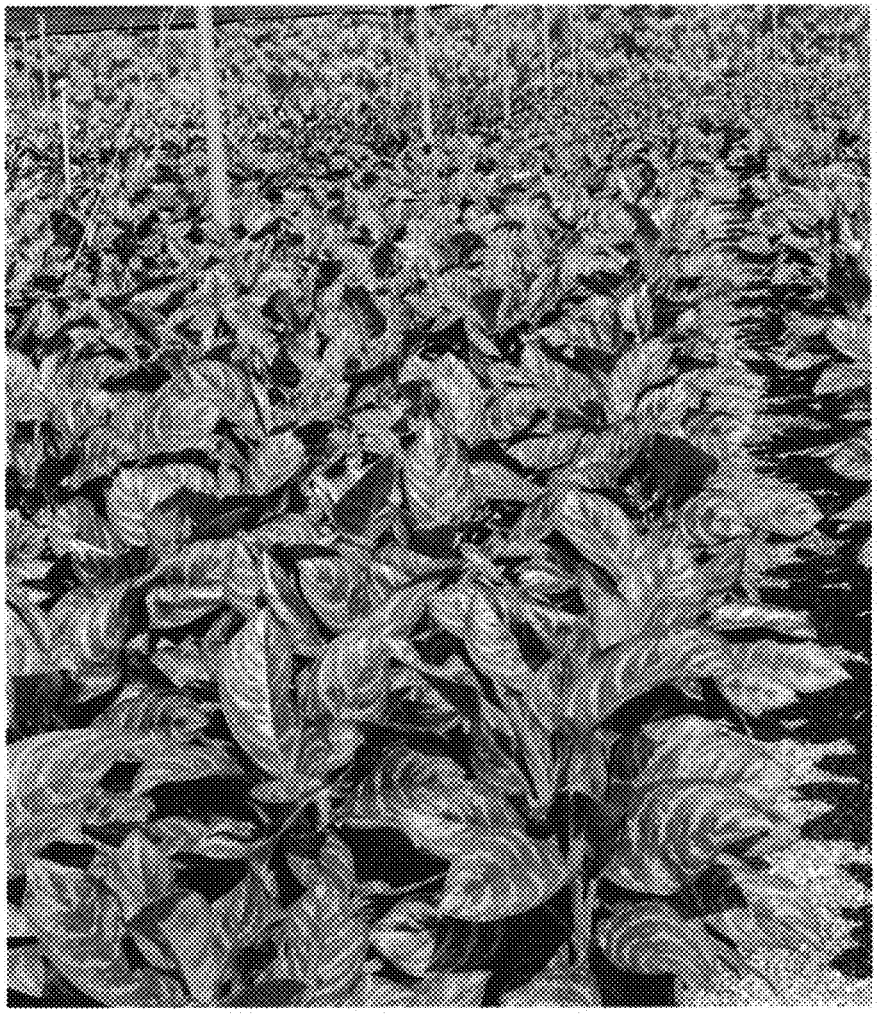

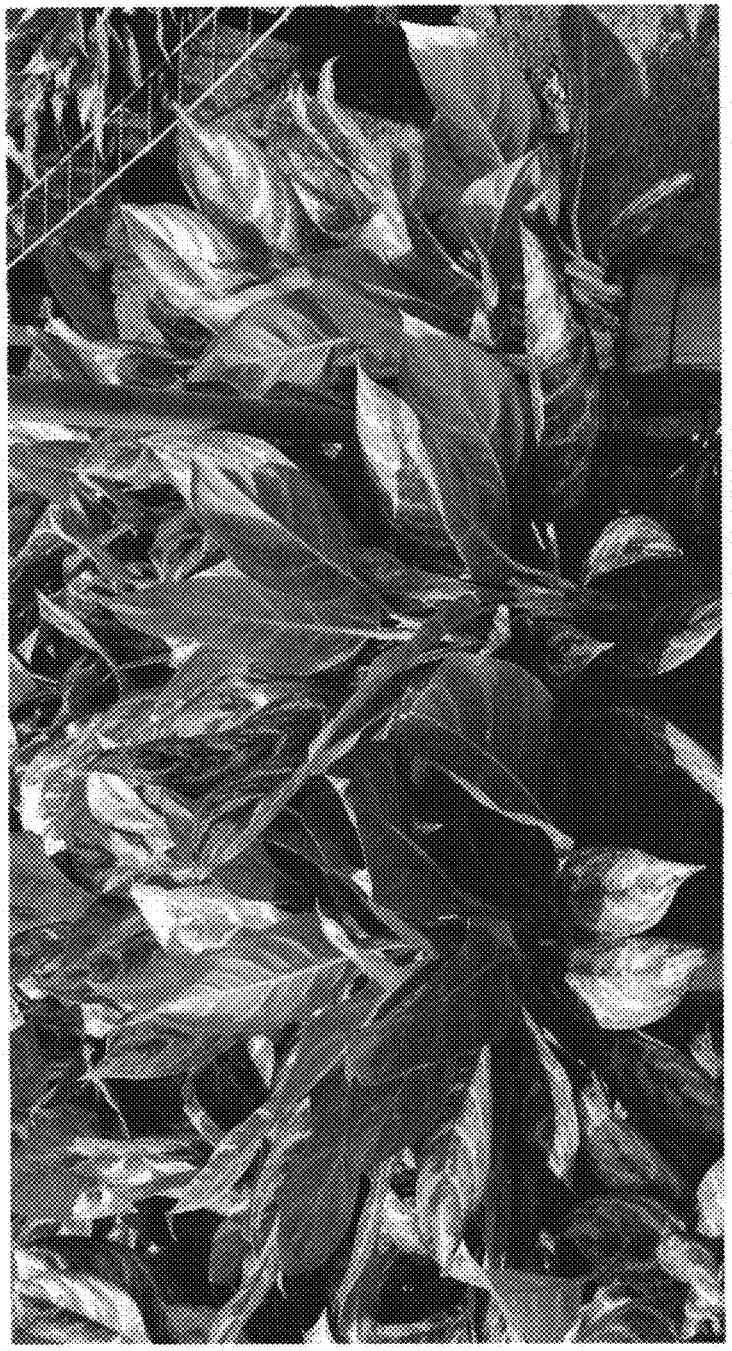

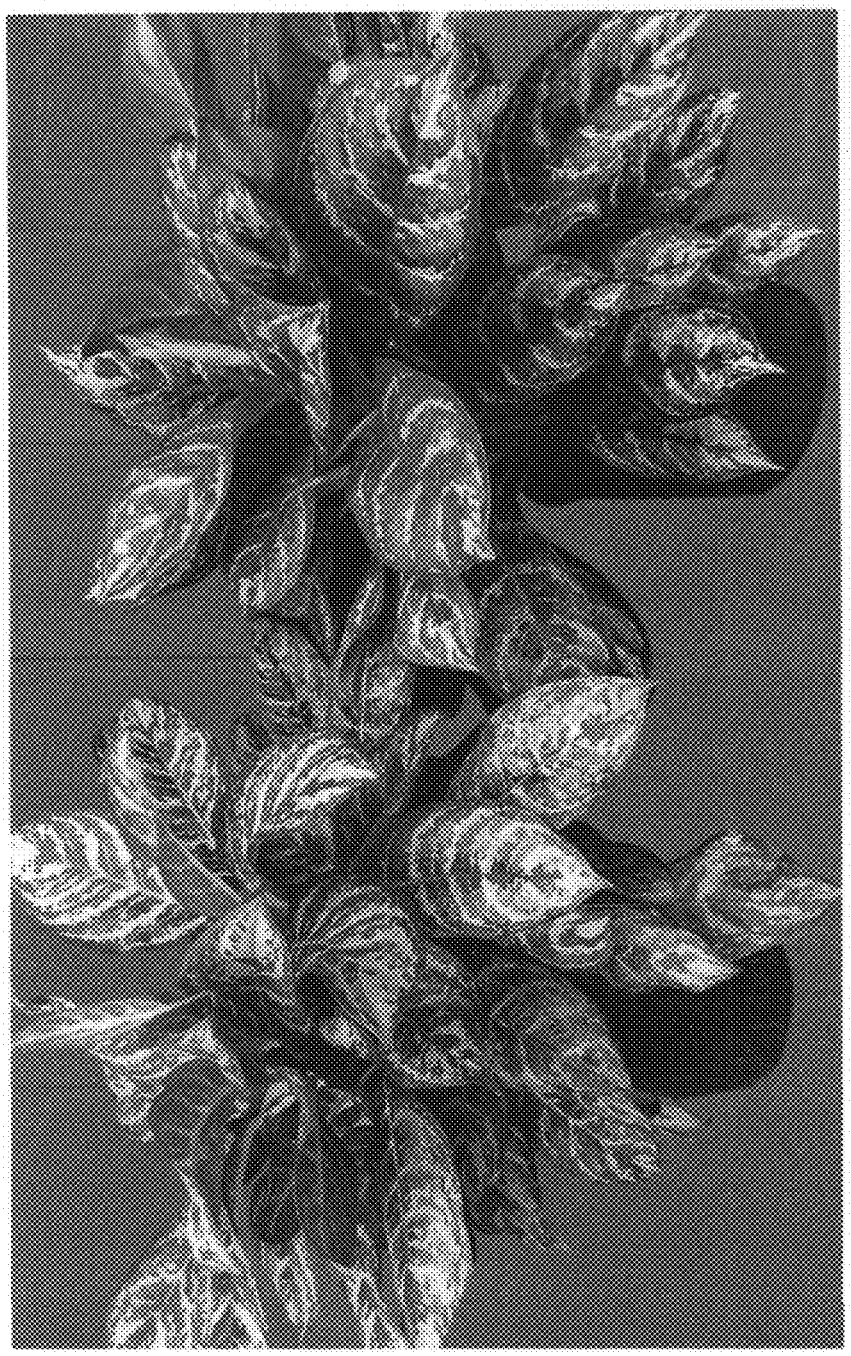

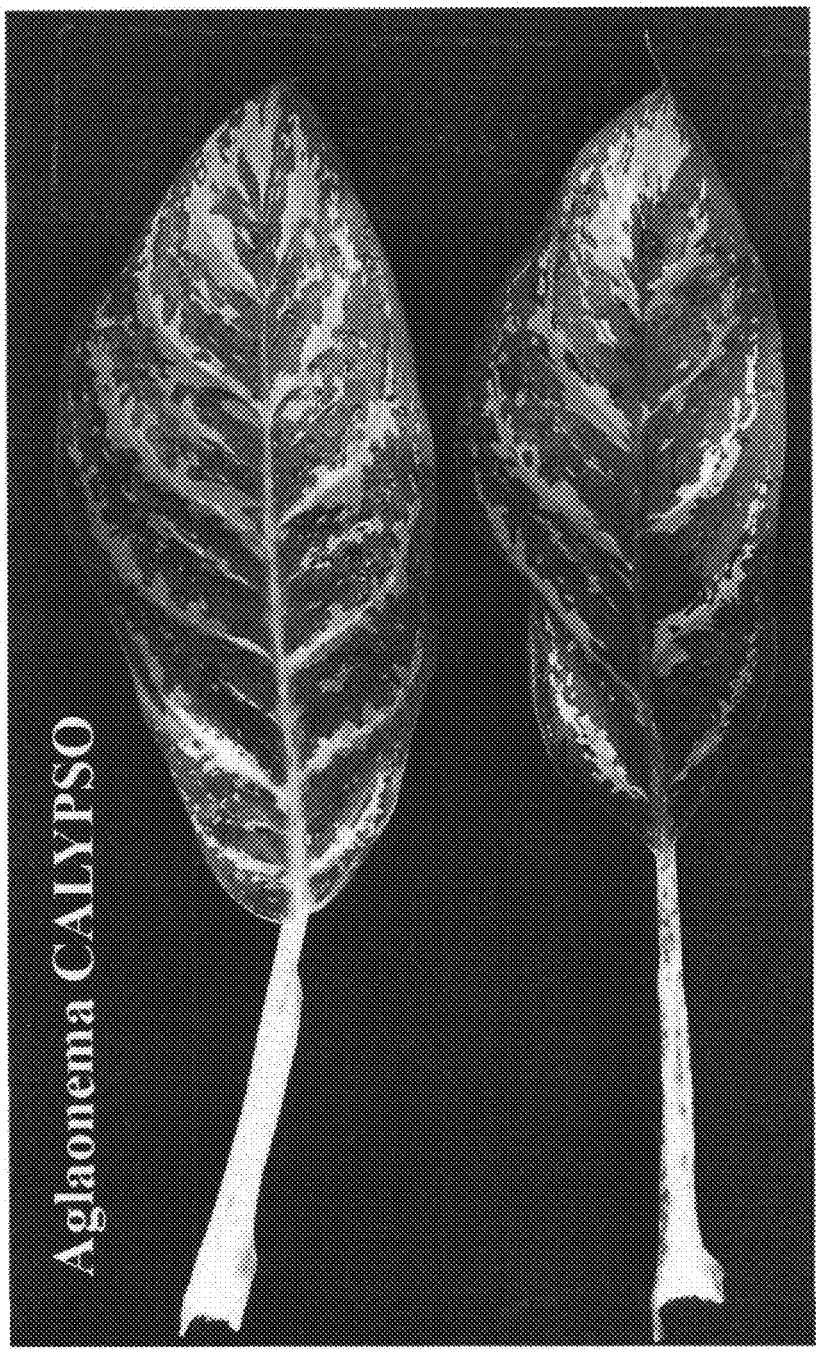
Aglaonema CALYPSO